(12) United States Patent
Corbacho

(10) Patent No.: US 8,210,167 B2
(45) Date of Patent: Jul. 3, 2012

(54) MANUALLY OPERATED MONODOSE NASAL SPRAYER

(75) Inventor: Hipolito P. Corbacho, Green Brook, NJ (US)

(73) Assignee: Corbco, Inc., Fort Meyers, FL (US)

( * ) Notice: Subject to any disclaimer, the term of this patent is extended or adjusted under 35 U.S.C. 154(b) by 1197 days.

(21) Appl. No.: 12/011,117

(22) Filed: Jan. 24, 2008

(65) Prior Publication Data

US 2008/0210229 A1    Sep. 4, 2008

Related U.S. Application Data

(63) Continuation-in-part of application No. 11/713,335, filed on Mar. 2, 2007.

(51) Int. Cl.
*A61M 11/00* (2006.01)
*A61M 15/00* (2006.01)
*A62B 7/00* (2006.01)

(52) U.S. Cl. ......... 128/200.22; 128/200.21; 128/200.24; 128/203.21; 128/203.12

(58) Field of Classification Search ............. 128/200.14, 128/200.21–200.23, 203.21
See application file for complete search history.

(56) References Cited

U.S. PATENT DOCUMENTS

| | | | |
|---|---|---|---|
| 3,934,585 A | 1/1976 | Maurice | |
| 4,474,314 A * | 10/1984 | Roggenburg, Jr. | 222/494 |
| 4,944,430 A | 7/1990 | Graf et al. | |
| 5,238,156 A | 8/1993 | Andris | |
| 5,267,986 A | 12/1993 | Py | |
| 5,401,259 A | 3/1995 | Py | |
| 5,546,932 A * | 8/1996 | Galli | 128/203.15 |
| 5,613,957 A | 3/1997 | Py | |
| 5,685,869 A | 11/1997 | Py | |
| 5,979,711 A | 11/1999 | Fuchs et al. | |
| 6,033,384 A | 3/2000 | Py | |
| 6,302,101 B1 | 10/2001 | Py | |
| 6,394,317 B1 * | 5/2002 | Faughey et al. | 222/309 |
| 6,419,663 B2 | 7/2002 | Harrold | |
| 6,877,672 B2 * | 4/2005 | Stihl | 239/8 |
| 6,997,219 B2 | 2/2006 | Py et al. | |
| 7,000,806 B2 | 2/2006 | Py et al. | |
| 7,407,494 B2 * | 8/2008 | Bostrom et al. | 604/207 |
| 2005/0098172 A1 * | 5/2005 | Anderson | 128/200.23 |
| 2006/0006192 A1 * | 1/2006 | Smith et al. | 222/83 |
| 2006/0151629 A1 * | 7/2006 | Vedrine et al. | 239/329 |
| 2009/0005735 A1 * | 1/2009 | Wikner et al. | 604/131 |

* cited by examiner

*Primary Examiner* — Justine Yu
*Assistant Examiner* — Rachel Young
(74) *Attorney, Agent, or Firm* — Kenneth P. Glynn, Esq.; Deirdra M. Meagher, Esq.

(57) ABSTRACT

The sprayer device utilizes a friction held piston that fires automatically upon full depression of the firing cap. A user may procure a monodose of medicine by (i) unlocking a child resistant mechanism; (ii) applying compressive force against the firing cap to first compress the spring and then to push the piston out of a friction area such that the spring causes the distal end of the piston to break the medicine container to drive medicine through the spray nozzle. The device includes a tear-away child resistant outer locking mechanism. Different length stops meter the amount of medicine dispensed. A two cap plug cap on the proximal and distal ends of the medicine package act as pistons. A piercer attached to a proximal end of the monodose medicine package moves upwardly when the piston is fired to pierce the medicine package and to drive medicine through the spray nozzle.

20 Claims, 11 Drawing Sheets

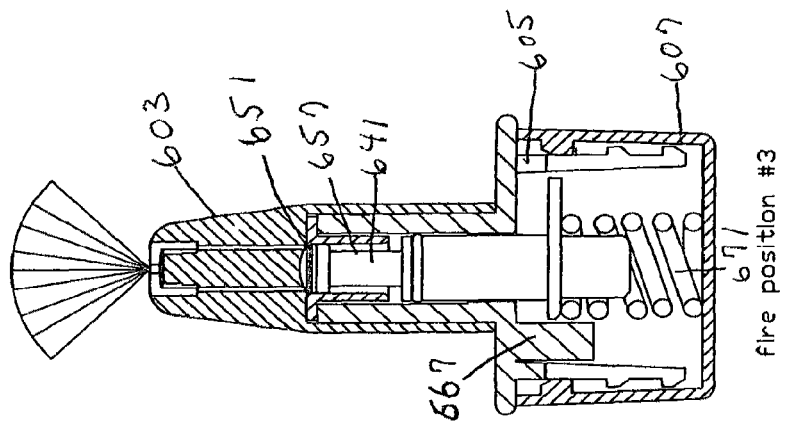
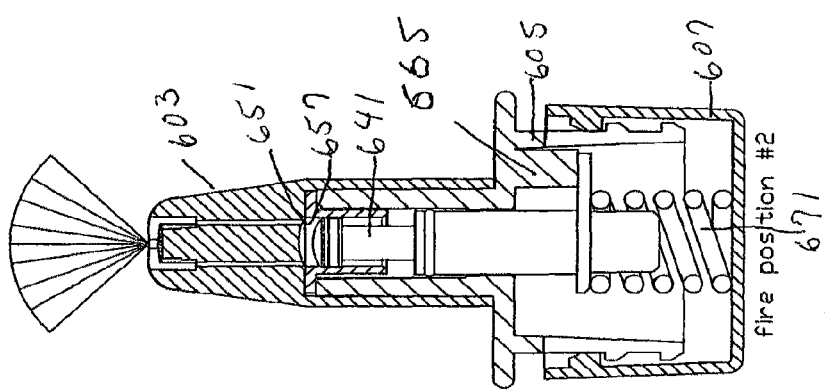
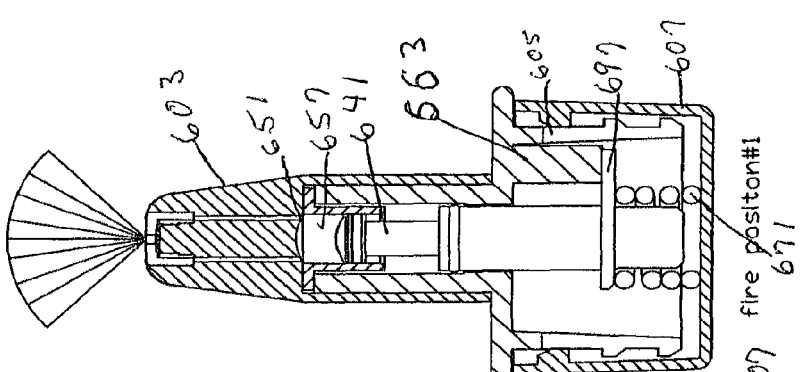
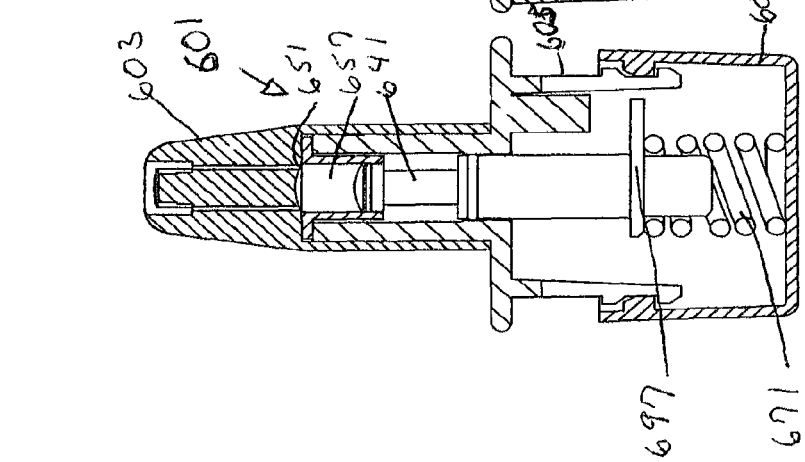

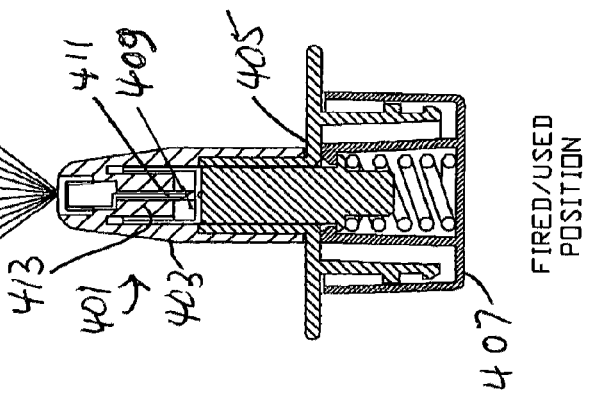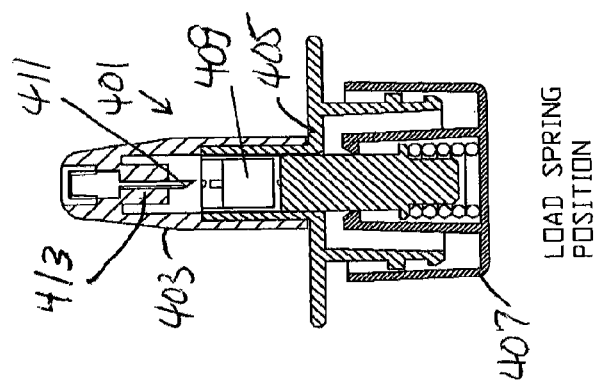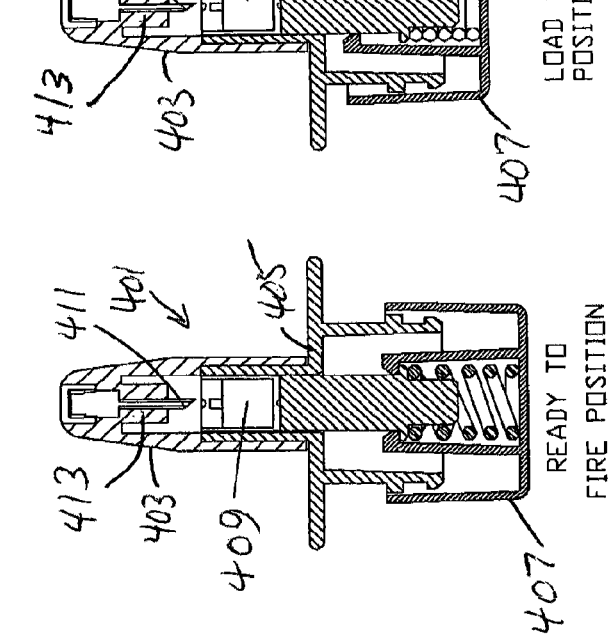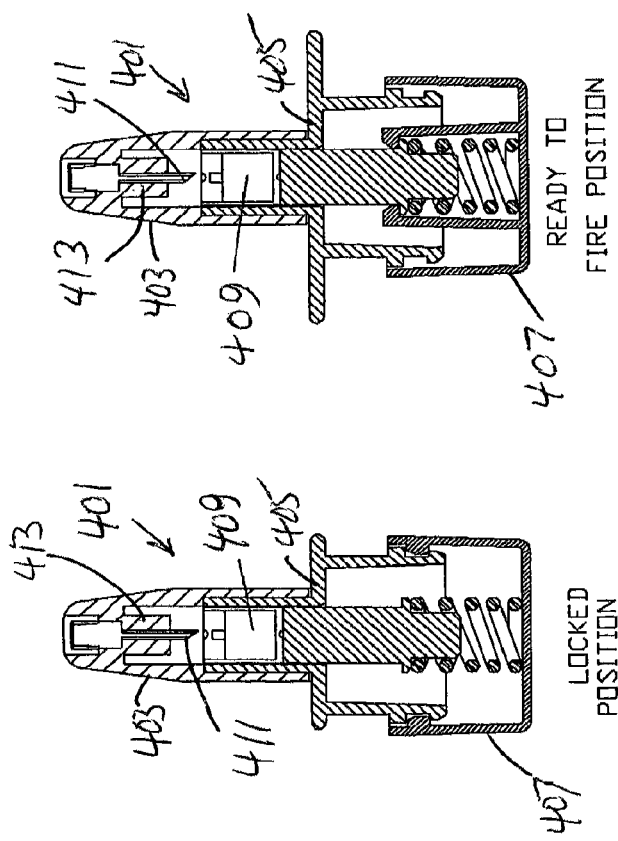

MANUALLY OPERATED MONODOSE NASAL SPRAYER

REFERENCE TO RELATED APPLICATION

This is a continuation-in-part of copending U.S. patent application Ser. No. 11/713,335 filed on Mar. 2, 2007, entitled "Monodose Nasal Sprayer" by the same inventor herein.

BACKGROUND OF INVENTION a. Field of Invention

The invention relates generally to nasal sprayers and, more particularly, to nasal sprayers that deliver a single dose that is user independent as to dosage amount and dosage speed of delivery to yield a consistent, predetermined dose and profile spray.

b. Description of Related Art

The following patents are representative of sprayers:

U.S. Pat. No. 7,000,806 B2 to Daniel Py et al. describes a dispenser for dispensing a fluid which includes a rigid vial that has a main fluid chamber containing a fluid, and a pump assembly that is in fluid communication with the main fluid chamber and is configured to dispense a predetermined quantity of fluid from the main fluid chamber. A flexible bladder is provided which is located within the main fluid chamber and is configured to expand to fill the ullage created within the main fluid chamber during dispensing of fluid by the pump assembly. The resilient bladder tends to force itself outwardly toward the rigid vial and, in turn, increases the pressure within the main fluid chamber in comparison to the interior of the bladder to thereby prevent the ingress of air or vapors through the bladder or otherwise into the main fluid chamber.

U.S. Pat. No. 6,997,219 to Daniel Py et al. describes a dispenser for holding multiple doses of fluids or other substances, and for dispensing the substances, which has a vial, a flexible bladder received within the vial, and a variable volume storage chamber formed between the bladder and vial. A filling valve is coupled in fluid communication with the storage chamber and defines a normally closed, fluid-tight position hermetically sealing the storage chamber from the ambient atmosphere, and an open position allowing the passage of fluid through the valve both to evacuate the storage chamber and to introduce fluid through the valve to fill the storage chamber. A pump is coupled in fluid communication with the storage chamber for pumping fluids out of the storage chamber. A dispensing valve is coupled in fluid communication with the pump and defines a normally closed, fluid-tight position preventing the passage of fluid out of the dispenser, and an open position for dispensing pumped fluid therethrough. The sealed, empty dispenser is sterilized, such as by applying gamma radiation thereto. Then, the sterilized, sealed, empty dispenser is filled with fluid by engaging the filling valve with an evacuating/dispensing member to evacuate the storage chamber, and by introducing fluid from the filling member through the open filling valve and into the storage chamber. The filling member is withdrawn from the valve, and a spring moves the valve to a closed position to hermetically seal the fluid within the dispenser.

U.S. Pat. No. 6,419,663 B2 to John E. Harrold describes the present invention mechanically propelled, liquid metered dispenser which includes a main housing with liquid storage and a liquid advancing component for either allowing liquid to flow out or assisting in the flow of liquid out of the main housing by exerting pressure, into a metered dosage dispensing chamber in response to a loading movement of a cocking mechanism. The chamber has an inlet connected to the main housing with a one-way valve to only permit flow of liquid into the chamber. The chamber also has an outlet orifice for dispensing liquid therefrom in a metered amount. The chamber has a reciprocal plunger and has a load and release component connected to it, which includes a cocking mechanism is functionally connected to the plunger so as to move in harmony therewith, or, more preferably, to move a relatively short distance relative to the distance traveled by the cocking mechanism.

U.S. Pat. No. 6,302,101 B1 to Daniel Py describes a pump type dispenser for dispensing predetermined doses of medicament in droplets or in spray form to the nasal area which incorporates a rigid vial for medicament, and expandable pouch located within the rigid vial, a nasal screen, a one-way actuation mechanism, a one-way valve mechanism in the nozzle area and a spring element, both the valve mechanism and the spring element being formed as integral portions of the pump body. The nasal screen aligns the dispenser nozzle with the nasal passage and also allows the user to discreetly hide the nasal area from the public view. The one-way valve mechanism in the nozzle area ensures a one-way movement of medicament from the dispenser, thereby preserving substantially perfect sterility of the medicament in the dispenser regardless of the environment surrounding the dispenser, without requiring the use of preservatives. The one way actuation mechanism enables the user to load and dispense a uniform quantity of medicament with a uniform actuation force and speed via a single continuous motion of the actuation mechanism upon application of a very small force on the actuation trigger mechanism by the user. By preventing the pump mechanism from being left in a loaded state for a prolonged period of time, the one-way actuation mechanism prevents the spring element from experiencing the "fatigue" phenomenon. The rigid vial/expandable-pouch combination facilitates improved long term use, as well as uniformity of dosage independent of the pump orientation.

U.S. Pat. No. 6,033,384 to Daniel Py describes a medicament-dispensing system which includes a cartridge for housing and actuating an accordion-like vial-dispenser for dispensing a calibrated amount of medicament by means of a single actuation motion which sequentially loads the vial-dispenser and dispenses the loaded medicament. The vial-dispenser has a front bellows portion, a rear bellows portion, an internal piston mechanism, a medicament storage chamber and a dosage cavity. The cartridge has a trigger mechanism which acts in concert with a notched lever and a wedge-shaped arm internally located in the cartridge to sequentially load the dosage cavity with medicament and discharge it. Depression of the trigger mechanism simultaneously extends, by means of the notched lever, the front bellows portion and compresses the rear bellows portion to load the dosage cavity with medicament. Once the notched lever has extended the front bellows portion a predetermined distance, the notched lever is disengaged form the front bellows portion by the wedge-shaped arm extending from the rear wall of the housing, thereby releasing the front and rear bellows portions, along with the internal piston mechanism, to return to original position and force the medicament from the dosage cavity via a nozzle of the vial-dispenser.

U.S. Pat. No. 5,979,711 to Karl-Heinz Fuchs et al. describes that in a device suitable for discharging media or at least one springly deformable component consists of a copolymer produced with a co-catalyst such as titanocen, more particularly an ethylene α-olefine copolymer which may also be improve as regards its resiliency by gamma irradiation. In a spiral spring produced from this or a similar plastics material axially adjacent spiral sections are directly integrally connected to each other not only via the spiral but also along the circumference of the spring.

U.S. Pat. No. 5,685,869 to Daniel Py describes an apparatus that is used to apply medicament to an eye and stores the medicament in a medicament chamber. A nozzle is coupled in fluid communication with the medicament chamber and is formed by an outer nozzle portion and an inner nozzle portion received within the outer nozzle portion. A seam is formed by the interface of the inner nozzle portion and the outer nozzle portion and is normally in a closed position to prevent the passage of medicament through the nozzle. The seam opens in response to the flow of medicament of sufficient pressure into the seam to permit the passage of medicament through the nozzle for release into the eye.

U.S. Pat. No. 5,613,957 to Daniel Py describes an apparatus that is used to apply medicament to an eye and stores the medicament in a medicament chamber. A nozzle is coupled in fluid communication with the medicament chamber and is formed by an outer nozzle portion and an inner nozzle portion received within the outer nozzle portion. A tight interface is defined between the inner nozzle portion and the outer nozzle portion and is normally in a closed position to prevent the passage of medicament through the nozzle. The interface opens in response to the flow of medicament of sufficient pressure into it to permit the passage of medicament through the nozzle for release into the eye.

U.S. Pat. No. 5,401,259 to Daniel Py describes a cartridge for actuating a piston-like or accordion-like dispenser-vial for applying a medicament to an eye. The cartridge includes a housing for holding the dispenser-vial and a telescoping cylinder for compressing the dispenser-vial in the longitudinal direction to actuate the vial. The cartridge includes a locking mechanism for locking the telescoping cylinder to restrict its movement and a lever mechanism for releasing the cylinder from the locked position so that a drop is released from the dispenser. The housing includes a finger for engaging the lower eyelid and exposing the conjunctival culde-sac.

U.S. Pat. No. 5,267,986 to Daniel Py describes a cartridge for actuating a piston-like or accordion-like dispenser-vial for applying medicament to an eye. The cartridge includes a housing for holding the dispenser-vial and a telescoping cylinder for compressing the dispenser-vial in the longitudinal direction to actuate the vial. The cartridge includes a locking mechanism for locking the telescoping cylinder to restrict its movement and a trigger mechanism for releasing the cylinder from the locked position so that a drop is released from the dispenser. The housing includes a finger for engaging the lower eyelid and exposing the conjunctival cul de sac.

U.S. Pat. No. 5,238,156 to Raimund Andris describes that in a metering and spray pump for liquid, low-viscosity and pasty substances, an elastic bellows is arranged between two plastic housing parts that are telescopingly movable relative to one another, connecting them. The bellows, acting as a discharge valve has, at one end, a valve annular wall that surrounds the generated surface of an inner annular discharge seat made in one piece with the first housing part in a sealing manner and such that it can be lifted off. As a suction valve the bellows has, at its other end, a valve annular wall which is in sealing and separable contact with the generated surface of a valve seat made in one piece with the second housing part such that it can be lifted off, and the medium to be pumped is drawn into the bellows through the valve seat. To guarantee high reliability of operation, especially good closing quality at weak valve opening forces, where the quality of closing can be tested even in the dry state, with the smallest possible number of simple and easy to assemble individual parts, the valve annular wall of the discharge valve and the valve annular wall of the suction valve, which valve annular wall is provided with a closed front wall, are each is contact with conical or hemispherical generated surfaces, wherein both valve annular walls are connected to the bellows both radially elastically and elastically movable in the axial direction.

U.S. Pat. No. 4,944,430 to Lothar Graf et al. describes a vacuum-tight and pressure-tight closed storage space in a container that is constructionally combined with a thrust piston pump projecting thereinto and a drag piston slideably guided therein and in the initial position of the thrust piston pump is hermetically sealed by an exhaust valve mechanically closed in forcibly controlled manner. The drag piston is adapted to the thrust piston pump in such a way that the storage space can be emptied substantially free with the thrust piston pump.

U.S. Pat. No. 3,934,585 to David M. Maurice describes a method and apparatus for applying therapeutic eye drops to the eye by metering a predetermined volume of fluid and rapidly applying a pressure to one end of the metered fluid for forcing the fluid from a nozzle of means defining a small passageway such as an open ended tube as a droplet having sufficient velocity to travel a generally horizontal distance in space to the eye. Unit dose application and multiple dose application are included and provision is made for preventing anticipatory blinking of the eye during self-administration.

Notwithstanding the prior art, the present invention is neither taught nor rendered obvious thereby.

SUMMARY OF INVENTION

The present invention is a monodose nasal sprayer device that eliminates the usual uncertainties of nasal sprayers, to wit, the speed of depression that affects the size and shape (profile) of the spray which in turn affects the efficacy of delivery; and the length of depression of the a typical nasal spray pump mechanism that affects the amount of dosage. These variables can have adverse affects on the proper treatment of a nasal condition and are completely eliminated by the present invention. Thus, the present invention has been developed to drive medicine through the spray nozzle in a manner that is user independent as to dosage amount and dosage speed of delivery to yield a consistent, predetermined dosage and a consistent predetermined profile spray.

The present invention includes an elongated main housing, a central member and a firing cap, as well as internal components. The main housing has a distal end adapted for partial insertion into one of a human nasal cavity and an animal nasal cavity and has a proximal end adapted to receive and hold the breakable monodose medicine package-supporting central member. The elongated main housing has a spray discharge nozzle located at its distal end, and it has a medicine-receiving chamber connected to the nozzle and biased toward the breakable monodose medicine package-supporting central member.

The central member is a breakable medicine package-supporting central member is connected to the proximal end of the elongated main housing. The connection may be permanent or removable, and it may be threaded, heat welded, snap fitted or otherwise connected and the central unit may be connect into the inside of the main housing, or vice versa. The central member has a distal end adapted to support a breakable monodose medicine package so as to be positioned at the chamber, and has a piston shaft with a piston-engaging high friction area end and a piston-releasing area distal end. A piston is located in the piston shaft, the piston having a medicine container breaking distal end, having a central area with a high friction engaging surface to engage the proximal end of the piston shaft and having an extended proximal end functionally connected to a firing cap. A firing cap is connected to the proximal end of the central member and is moveable toward the distal end of the central member by compressive force. The firing cap has a piston-receiving cavity and a drive spring located in the cavity and the extended proximal end of the piston is functionally connected to the spring. A finger support means is located on the outside of one of the main housing and the central member. A child resistant inner locking mechanism is connected to at least one of the central member and the firing cap that is unlockable and, when locked, prevents movement of the firing cap toward the distal end of the central member, and permits movement of the firing cap toward the distal end of the central member when the locking member is unlocked. A child resistant outer locking mechanism is connected to the firing cap and the central member, and is adapted to prevent movement of the firing cap. The child resistant outer locking mechanism is a tear away system including a connection means for connecting said firing cap to said central member. The outer locking mechanism connection means includes a perforated tab surrounding a circumference of at least one of said firing cap and said central member.

An essential feature is that the force required to overcome the frictional force between the high friction engaging surface of the piston and the piston shaft is greater than the force required to compress the spring. A user may procure a monodose of medicine with the device when loaded with a breakable monodose medicine package by (i) removing the child resistant outer locking mechanism so that its position is unlocked; (ii) moving the inner child resistant locking mechanism from its locked position to its unlocked position; (iii) placing fingers in front of the finger support means and applying compressive force against the firing cap to move the firing cap towards the central member so as to first compress the spring before moving the piston, and to move the firing cap closer toward the central member to push the piston out of the piston engaging friction area of the shaft so as to sufficiently reduce friction such that the spring automatically and with significant celerity, fires the piston and causes the distal end of the piston to puncture the breakable monodose medicine package. This automatically drives medicine therefrom to and through the spray nozzle in a manner that is user independent as to dosage amount and dosage speed of delivery to yield a consistent, predetermined speed of delivery and a predetermined profile spray.

In some preferred embodiments, the manually operated monodose nasal sprayer includes a piercer attached to a proximal end of the single use monodose medicine package wherein when the piston is fired the piercer moves upwardly through the single use monodose medicine package to pierce the monodose medicine package and to drive medicine therefrom to and through the nozzle.

In some preferred embodiments, the present invention monodose nasal sprayer device piston shaft and the piston have corresponding circular peripheries from a top view.

In some preferred embodiments of the present invention monodose nasal sprayer device, the distal end of the central member and the proximal end of the main housing have corresponding screw components and the central member distal end and the main housing proximal end are screwed to one another.

In some preferred embodiments of the present invention monodose nasal sprayer device, the screw components include a one way locking thread stop so that the distal end of the central member and the proximal end of the main housing cannot be unscrewed once screwed together.

In some preferred embodiments of the present invention monodose nasal sprayer device, the proximal end of the piston includes a flange that fits atop the spring and fits into the firing cap cavity.

In some preferred embodiments of the present invention monodose nasal sprayer device, the child resistant locking mechanism is a rotating locking mechanism with a first position being a lock position to inhibit advancement of the firing cap and a second position being an unlock position to permit advancement of the firing cap, the second position being located at an arc of a predetermined distance from the first position.

In some preferred embodiments of the present invention monodose nasal sprayer device, the child resistant locking mechanism includes a protrusion on the firing cap and a receiving track on the central member such that when the protrusion is positioned in alignment with the receiving track, it is in its unlock position and the firing cap may be advanced toward the central member.

In some preferred embodiments of the present invention monodose nasal sprayer device, the device further includes a breakable monodose medicine package mounted on the distal end of the central member and at least partially projecting into the chamber.

In some preferred embodiments of the present invention monodose nasal sprayer device, at least one of the piston and the shaft includes at least one friction ring.

In some preferred embodiments of the present invention monodose nasal sprayer device, the distal end of the central member and the proximal end of the main housing have corresponding snap-together components and the central member distal end and the main housing proximal end are snapped into one another.

In another preferred embodiment of the present invention monodose nasal sprayer device, the device includes: a.) an elongated main housing having a distal end adapted for partial insertion into a one of human nasal cavity and an animal nasal cavity and having a proximal end adapted to receive and hold a monodose medicine package-supporting central member. The elongated main housing has a spray discharge nozzle located at its distal end, the elongated main housing having medicine-receiving chamber connected to said nozzle and biased toward the monodose medicine package-supporting central member;

b.) the medicine package-supporting central member being connected to the proximal end of the elongated main housing, the central member having a distal end adapted to support a monodose medicine package so as to be positioned at the chamber, and having a piston shaft with a piston-engaging high friction area end and having a piston-releasing area distal end;

c.) a piston located in the piston shaft, the piston having a medicine container breaking distal end, having a central area with a high friction engaging surface to engage the proximal end of the piston shaft and having an extended proximal end functionally connected to a firing cap;

d.) a firing cap connected to said proximal end of the central member and being moveable toward said distal end of the central member by compressive force, the firing cap having a piston-receiving cavity and a drive spring located in the cavity, the extended proximal end of the piston being functionally connected to the spring;

e.) finger support means located on the outside of one of the main housing and the central member;

f.) a child resistant inner locking mechanism connected to at least one of the central member and the firing cap that is unlockable and, when locked, prevents movement of the firing cap toward the distal end of the central member, and permits movement of the firing cap toward the distal end of the central member when the locking member is unlocked; and g.) a plurality of dosage choice stops extending from the central member so that each stop may intersect a bar attached to the spring when the spring is decompressed and a corresponding monodose indicator is selected, the stops being different lengths adapted to meter a different predefined monodose and to stop movement of the spring such that when spring movement is stopped by a longer length stop the piston penetrates into a shorter distance within the monodose package thereby providing for less medicine to be dispensed when the monodose medicine package is punctured and when the spring movement is stopped by a shorter length stop the piston penetrates into a longer distance within the monodose package thereby providing for more the medicine to be dispensed when the monodose medicine package is punctured;

wherein the force required to overcome the frictional force between the high friction engaging surface of the piston and the piston shaft is greater than the force required to compress the spring; and, wherein a user may procure a monodose of medicine with the device when loaded with a monodose medicine package by (i.) moving the inner locking mechanism from its locked position to its unlocked position; (ii) selecting a metered monodose amount by rotating the central member to a monodose amount indicator so that the stop for the selected metered monodosage amount may intersect the bar of the spring; (ii) placing fingers in front of the finger support means and applying compressive force against the firing cap to move the firing cap towards the central member so as to compress the spring and to move the firing cap closer toward the central member to push the piston out of the piston engaging friction area of the shaft so as to sufficiently reduce friction such that the spring automatically and with significant celerity, fires the piston and causes the distal end of the piston to puncture the monodose medicine package and to drive medicine therefrom to and through the spray nozzle in a manner that is user independent as to dosage amount, once selected, and dosage speed of delivery to yield a consistent, predetermined profile spray.

In another preferred embodiment, a monodose nasal sprayer device comprises:

a.) an elongated main housing having a distal end adapted for partial insertion into one of a human nasal cavity and an animal nasal cavity and having a proximal end adapted to receive and hold a single use monodose medicine package-supporting central member, the elongated main housing having a spray discharge nozzle located at its distal end, the elongated main housing having medicine-receiving chamber connected to the nozzle and biased toward the single use monodose medicine package-supporting central member; b b.) the single use medicine package-supporting central member being connected to the proximal end of the elongated main housing, the central member having a distal end adapted to support a single use monodose medicine package so as to be positioned at the chamber, and having a piston shaft with a piston-engaging high friction area end and having a piston-releasing area distal end;

c.) a proximal end plug cap piston located in the piston shaft, the proximal end plug cap piston having a medicine container breaking distal end plug cap piston, having a central area with a high friction engaging surface to engage the proximal end of the piston shaft and having an extended proximal end functionally connected to a firing cap;

d.) a firing cap connected to the proximal end of the central member and being moveable toward the distal end of the central member by compressive force, the firing cap having a piston-receiving cavity and a drive spring located in the cavity, the extended proximal end of the piston being functionally connected to the spring;

e.) finger support means located on the outside of one of the main housing and the central member;

f.) a child resistant inner locking mechanism connected to at least one of the central member and the firing cap that is unlockable and, when locked, prevents movement of the firing cap toward the distal end of the central member, and permits movement of the firing cap toward the distal end of the central member when the locking member is unlocked; and g.) the single use monodose medicine package including the proximal end plug cap piston and the distal end plug cap piston wherein when the firing cap is fired and the spring pushes the proximal end plug cap piston into the distal end plug cap piston thereby driving the medicine through the spray nozzle;

wherein the force required to overcome the frictional force between the high friction engaging surface of the proximal end plug cap piston and the piston shaft is greater than the force required to compress the spring; and, wherein a user may procure a monodose of medicine with the device when loaded with a single use monodose medicine package by (i.) moving the inner locking mechanism from its locked position to its unlocked position; (ii) placing fingers in front of the finger support means and applying compressive force against the firing cap to move the firing cap towards the central member so as to compress the spring and to move the firing cap closer toward the central member to push the proximal end plug cap piston out of the piston engaging friction area of the shaft so as to sufficiently reduce friction such that the spring automatically and with significant celerity, fires the piston and causes the distal end of the piston to force the proximal end plug cap to move as a piston through the single use monodose medicine package and to force the distal end plug cap to be removed from the plug and to move as a piston thereby driving the medicine therefrom to and through the spray nozzle in a manner that is user independent as to dosage amount and dosage speed of delivery to yield a consistent, predetermined profile spray.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings:

FIG. 1 illustrates a front cut view of one preferred embodiment of a present invention monodose nasal sprayer having a child resistant outer locking mechanism and a two plug cap;

FIG. 2 illustrates a front view of the child resistant outer locking mechanism, shown in FIG. 1;

FIG. 3 illustrates a front cut view of another embodiment of a present invention monodose nasal sprayer having a piercer for piercing a monodose medicine package;

FIGS. 4, 5, 6 and 7 illustrate another present invention embodiment wherein they show side cut views of the sprayer at different stages using a plurality of stops for metering different doses;

DETAILED DESCRIPTION OF THE EMBODIMENTS

Figure 1:
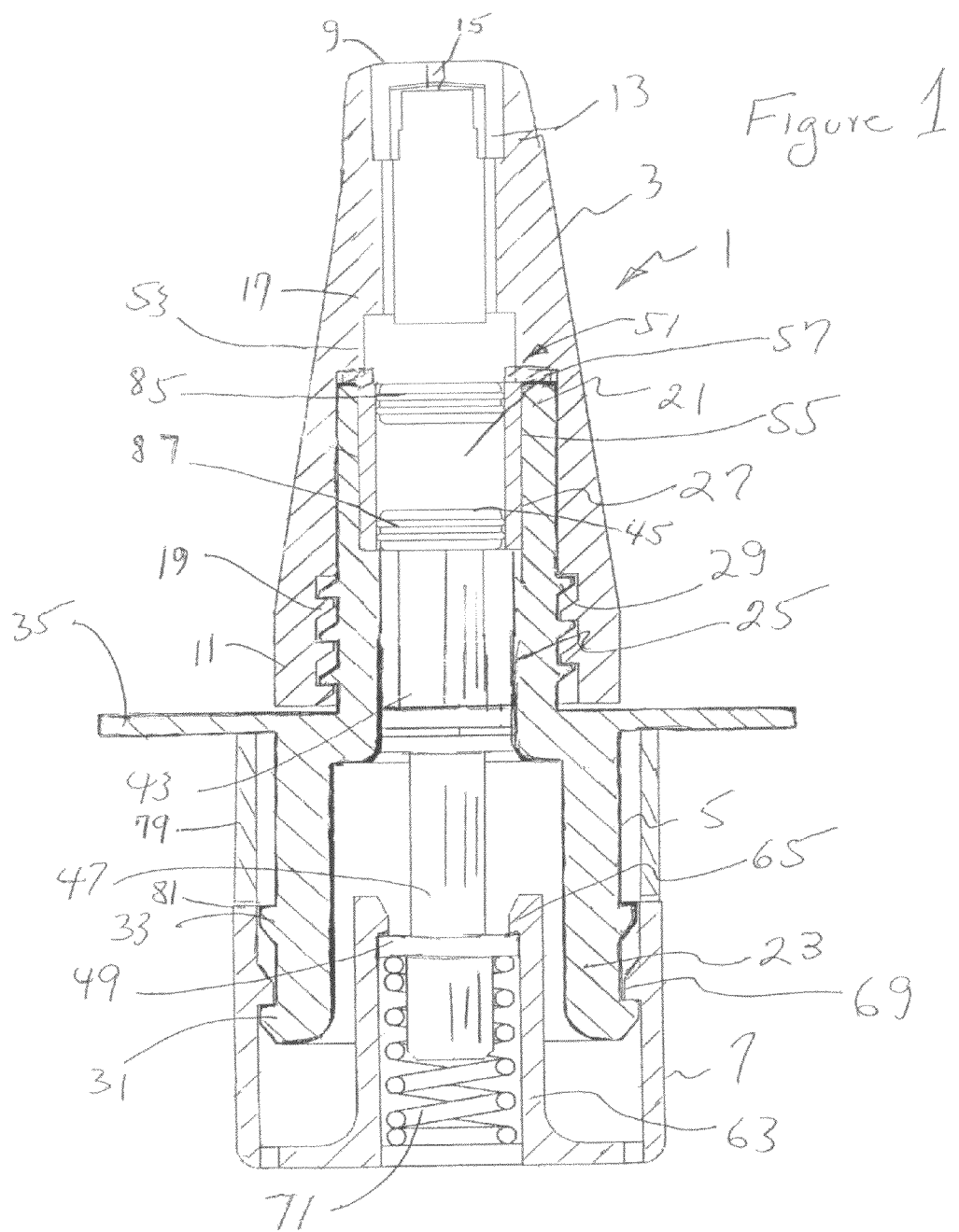

Referring now to the drawings, like reference numerals designate corresponding parts throughout the several views.

Figure 2:
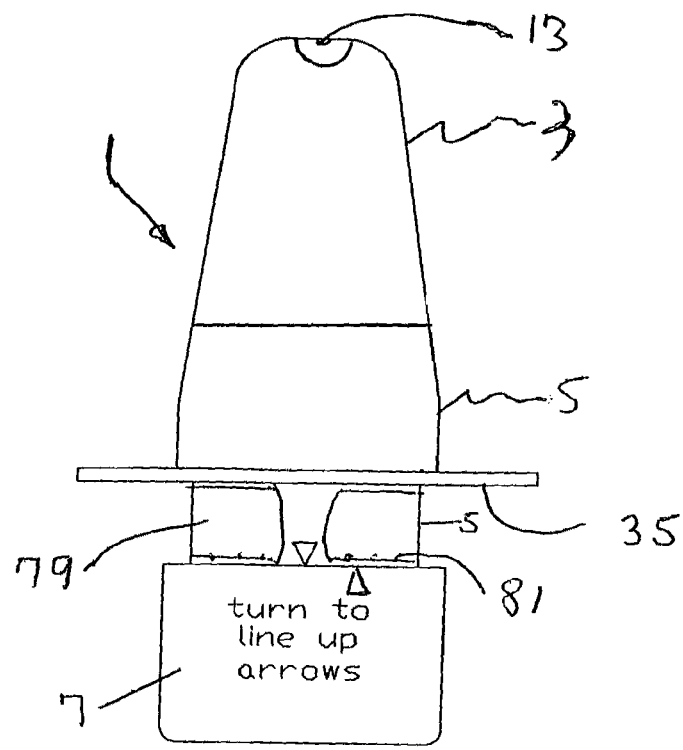

FIG. 1 illustrates a front cut view of one preferred embodiment of a present invention monodose nasal sprayer 1 having a child resistant outer locking mechanism 79 and a two plug cap 85 and 87 while FIG. 2 illustrates a front view of the child resistant outer locking mechanism 81 shown in FIG. 1. It includes an elongated main housing 3 having a distal end 9 adapted for partial insertion into one of a human nasal cavity and an animal nasal cavity. Main housing 3 also has a proximal end 11 adapted to receive and hold a single-use monodose medicine package-supporting central member 5. The elongated main housing 3 has a spray discharge mechanism 13 and nozzle 15 located at its distal end 9. It also has medicine-receiving chamber 17 connected to the nozzle 15 via spray discharge mechanism 13. Chamber 17 is biased toward the single-use monodose medicine package-supporting central member 5 and is adjacent to central member 5's medicine package support, as shown.

The single-use medicine package-supporting central member 5 is connected to the proximal end 11 of the elongated main housing 3. In this embodiment, the connection is via locking threads such as thread 19 on main housing 3 and thread 29 on central member 5. The central member 5 has a distal end 21 adapted to support monodose medicine package 51 so as to be positioned at (directly below) main housing chamber 17, as shown. Central member 5 also has a piston shaft 27 with a piston-engaging high friction area end 25 and has a piston-releasing area distal end 21. There is a piston 87, in this case, a plug cap, located in the piston shaft 27, with piston 87 having a medicine container breaking distal end 45, having a central area 43 with a high friction engaging surface to engage the proximal end of the piston shaft 25 and having an extended proximal end 47 with flange 49, functionally connected to firing cap 7. The piston 87 has one or more friction rings such as the rings of the distal end plug cap piston 87, but could have alternative or additional friction creating means, such as abraded areas, etched areas, molded three dimensional topography areas, friction creating sprays, coatings or layers, friction bands or combinations thereof. Firing cap 7 is connected to the proximal end 23 of the central member 5 and is moveable toward the distal end 21 of central member 5 by compressive force. The firing cap 7 has a piston-receiving cavity 63 and a drive spring 71 located in the cavity 63. The extended proximal end 47 of the piston 41 is functionally connected to the spring 71 as shown. Piston flange 49 is positioned under rim 65 and nests atop spring 71, as shown.

At the distal end of the monodose medicine package 51 there is a second plug cap 85 which also acts as a piston when the device is fired. Both plug caps 85 and 87 act as pistons when the firing cap 7 is fired and when the spring 71 pushes the proximal end plug cap piston 87 through the monodose medicine package 51 thereby pushing the distal end plug cap piston 85 to drive the medicine 57 through the nozzle 15.

The plug caps are preferably plastic caps with or without force fit mechanisms, e.g. friction rings. Alternatively, the caps may be combinations of plastic caps with foil seals, and in some embodiments, foil seals may replace one or more plastic caps and function as foil caps.

There is a finger support means 35 located on the outside of one of the main housing 3 and the central member 5. In this drawing, it is located on the outside of central member 5, but would be equally functional if located on the outside of main housing 3. A child resistant inner locking mechanism is connected to at least one of the central member 5 and the firing cap 7 that is unlockable and, when locked, prevents upward movement of the firing cap 7 toward the distal end 23 of the central member 5, and permits upward movement of the firing cap 7 toward the distal end 23 of the central member 5 when the locking member is unlocked. In this drawing the CR locking mechanism is hidden, but FIGS. 15 and 16 below show bottom view details of one such mechanism that could be used in this embodiment.

A post firing lock-up mechanism is connected to the central member 5 and the firing cap 7 such that, once the device has been fired and the firing cap 7 has been advanced forward (upward) toward the central member 5, this locking mechanism is activated and locks up so as to prevent movement of the firing cap 7 away from the distal end 23 of the central member 5. In this embodiment, the distal end 23 of central member 5 has two external protrusions 31 and 33 and firing cap 7 has an internal protrusion 69. (For purposes of this drawing, the protrusions are 360 degree full circle protrusions, but could be segmented or opposing pairs, or one component could be full circle and the other be segmented, e.g., protrusion 69 is full circle and protrusions 31 and 33 are arcs.)

The child resistant outer locking mechanism 79 is connected to the firing cap 7 and the central member 5 and is adapted to prevent movement of the firing cap 7. The outer locking mechanism 79 is a tear away system which includes a connection means 81 for connecting the firing cap 7 to the central member 5. In this case, the connection means is a perforated tab surrounding a circumference of a least one of the firing cap 7 and the central member 5.

An essential feature of this and all present invention embodiments relates to the relative forces between the piston and the spring. Specifically, the force required to overcome the frictional force between said high friction engaging surface of the base cap piston 87 and the piston shaft high friction area 25 is greater than the force required to compress spring 71. In this way, a user may procure a monodose of medicine with the device when loaded with a breakable monodose medicine package 51, in this case with base cap piston 87, top cap 85 and medicine 57. The user accomplishes the results by (i) removing the outer locking mechanism so that its position is unlocked; (ii) moving the outer locking mechanism from its locked position to its unlocked position; (iii) placing fingers in front of the finger support means and applying compressive force against the firing cap to move the firing cap towards the central member so as to compress the spring and to move the firing cap closer toward the central member to push the proximal end plug cap piston out of the piston engaging friction area of the shaft so as to sufficiently reduce friction such that the spring automatically and with significant celerity, fires the piston and causes the distal end of the piston to puncture the breakable monodose medicine package and to drive medicine therefrom to and through the spray nozzle in a manner that is user independent as to dosage amount and dosage speed of delivery to yield a consistent, predetermined profile spray. The post firing lock-up mechanism automatically locks the device after use so that it cannot be refired.

Figure 3:
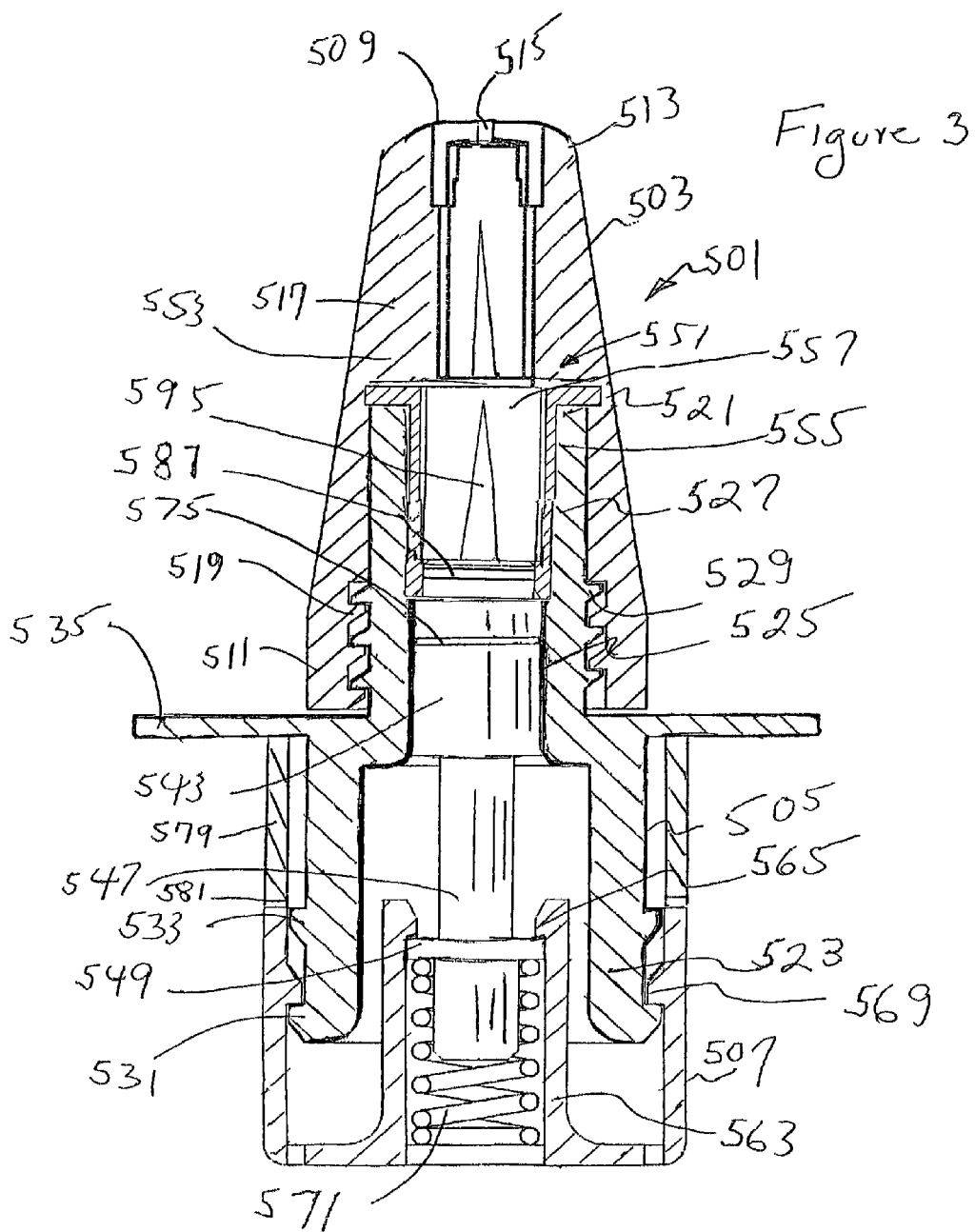

FIG. 3 illustrates a front cut view of another embodiment of a present invention monodose nasal sprayer 501 having a piercer 595 for piercing a monodose medicine package 51. Similar parts to those described and illustrated by FIG. 1 are similarly numbered, but beginning with "500" and are incorporated herein in by reference to the above. Attached to the proximal end plug cap piston 587 is a piercer 595. When the proximal end plug cap piston 587 is pushed by the force of the spring 571 when the cap 507 is fired, the piercer 595 is correspondingly moved to pierce the monodose medicine package 551 and drive the medicine 557 out through the nozzle 515.

Figure 8:
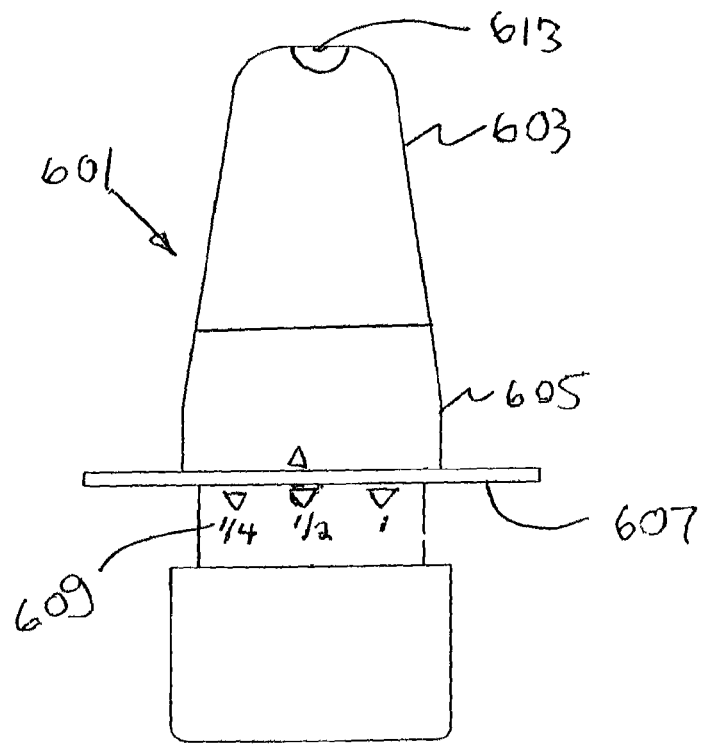
FIG. 8 shows a front view of the present invention embodiment of FIGS. 4, 5, 6 and 7.

FIGS. 4, 5, 6 and 7 illustrate another present invention embodiment wherein they show side cut views of the sprayer at different stages using a plurality of dosage choice stops 663, 665 and 667 for metering different doses while FIG. 8 shows a front view thereof. Similar parts to those described and illustrated by FIG. 1 are similarly numbered, but beginning with "600" and are incorporated herein in by reference to the above. In all of these Figures, sprayer 601 has the three feature components, namely, main housing 603, central member 605 and firing cap 607.

The plurality of dosage choice stops 663, 665 and 667 extend from said the central member 605 so that each stop 663, 665 and 667 may intersect a horizontal bar 697 attached to a spring 671. This occurs when the spring 671 is decompressed and a corresponding monodose indicator on the main housing 603 is selected. The selection for dosage choice is accomplished by rotating the central member 603 to a monodose relative amount indicator which allows one of the stops 663, 665 and 667 to align with said bar 697. The relative amounts are fractions for the percentage of the medicine desired. The stops 663, 665 and 667 are different lengths adapted to meter a different selected monodose of medicine by stopping movement of the spring 671 such that when spring movement is stopped by a longer length stop 663 a piston 641 penetrates into a shorter distance within a monodose package 651 thereby providing for less medicine to be dispensed when the monodose medicine package 651 is punctured and when the spring movement is stopped by a shorter length stop 665 the piston 641 penetrates into a longer distance within the monodose package 651 thereby providing for more medicine 657 to be dispensed when the monodose medicine package 657 is punctured.

Figure 9:
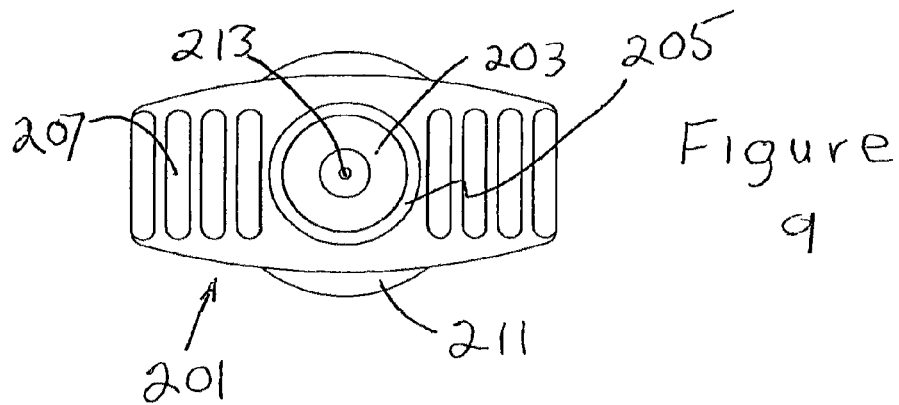
FIGS. 9, 10 and 11 show top, front and bottom views of yet another embodiment of a present invention monodose nasal sprayer.
Figure 10:
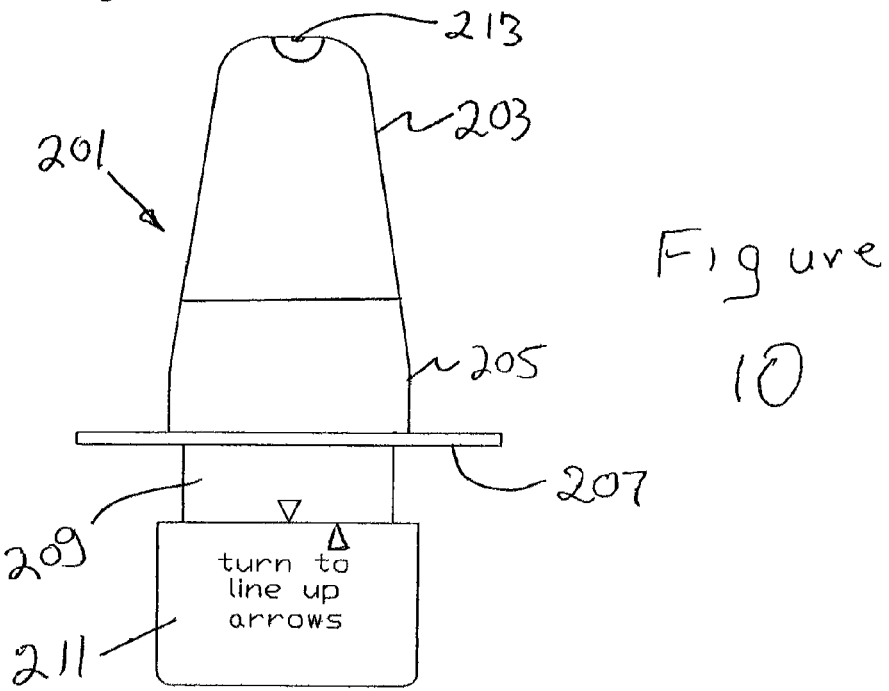
Figure 11:
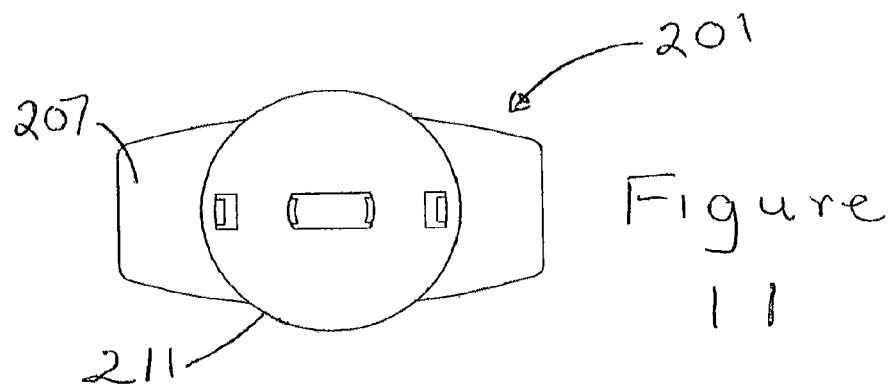
Figure 12:
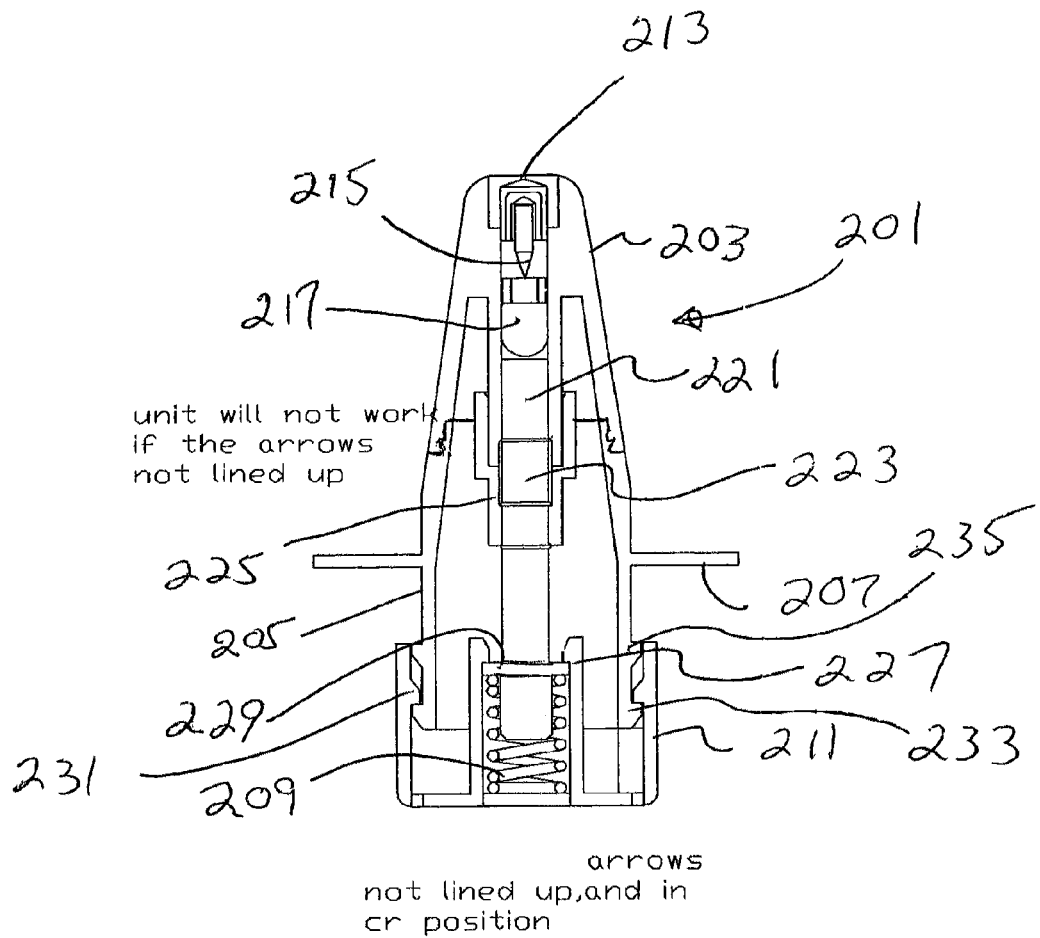
FIG. 12 shows the present invention monodose nasal sprayer of FIGS. 9, 10 and 11 in its rest position.
Figure 13:
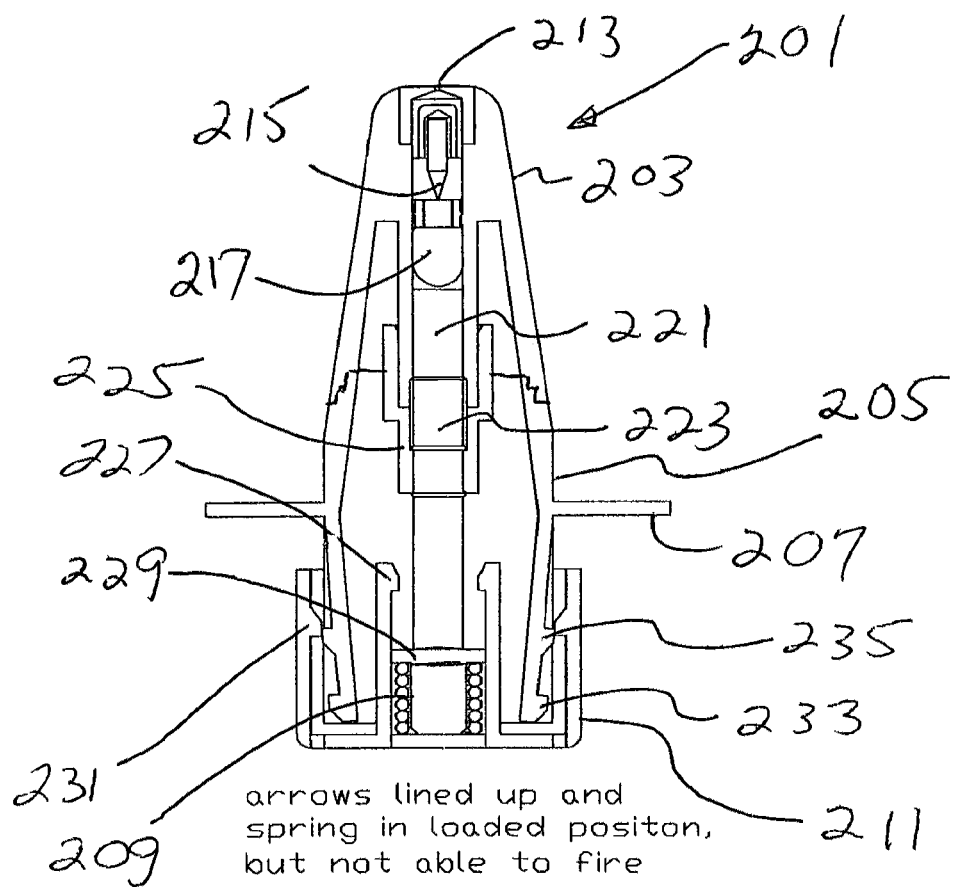
FIG. 13 shows the present invention monodose nasal sprayer of FIGS. 9, 10 and 11 in its fully compressed spring position (being squeezed)
Figure 14:
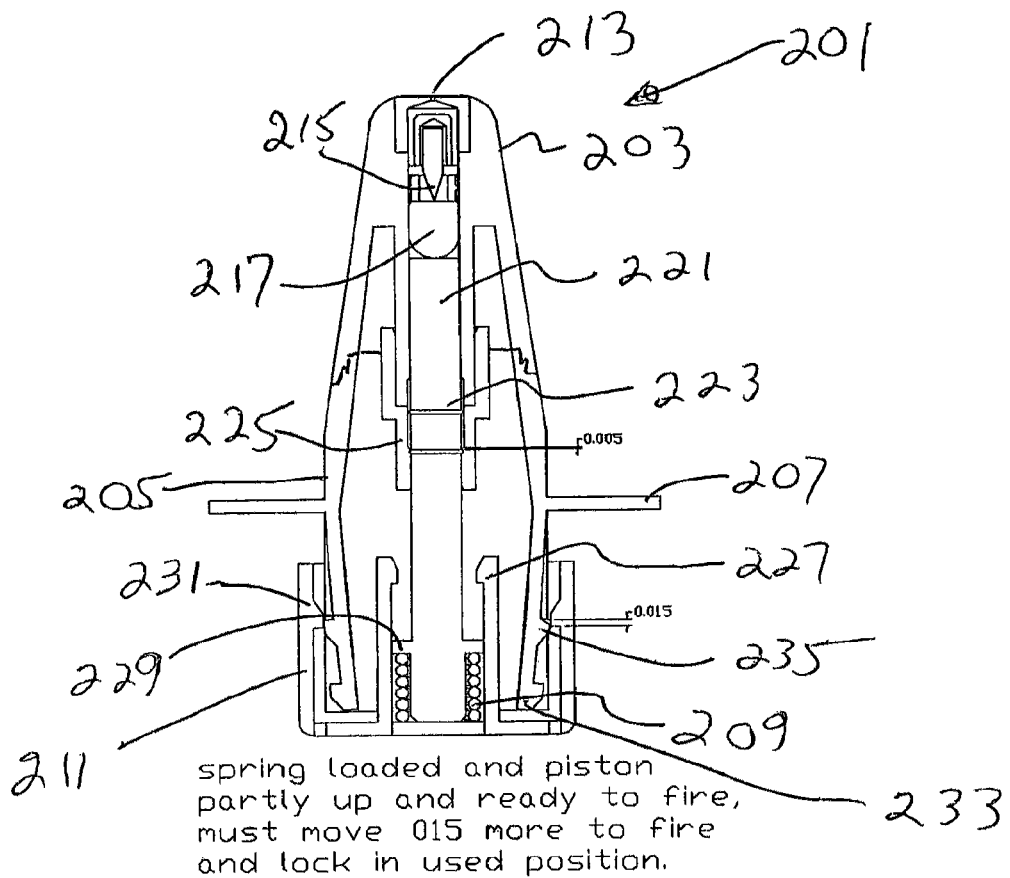
FIG. 14 shows the present invention monodose nasal sprayer of FIGS. 9, 10 and 11 in its fully compressed spring with advancing piston position (being squeezed)

FIGS. 9, 10 and 11 illustrate top, front and bottom views of yet another embodiment of a present invention monodose nasal sprayer 201. FIG. 12 shows the present invention monodose nasal sprayer 201 of FIGS. 9, 10 and 11 in its rest position. FIG. 13 shows the present invention monodose nasal sprayer 201 of FIGS. 9, 10 and 11 in its fully compressed spring position (being squeezed). And FIG. 14 shows the present invention monodose nasal sprayer 201 of FIGS. 9, 10 and 11 in its fully compressed spring with advancing piston position (being squeezed). All of these Figures have like numbered components and the Figures are discussed collectively.

Sprayer 201 includes an elongated main housing 203 having a distal end adapted for partial insertion into one of a human nasal cavity and an animal nasal cavity. Main housing 3 also has a proximal end adapted to receive and hold a breakable monodose medicine package-supporting central member 205. In this embodiment, the connection between the main housing 203 and the central member 205 is a force fit, as shown. The elongated main housing 203 has a spray discharge mechanism nozzle 213 located at its distal end and a medicine container piercing spike 215 extending downwardly therefrom into a chamber into which a medicine container is driven by the firing of the device and associated release of the piston. The medicine-receiving chamber is connected to the nozzle 213 via the spray discharge mechanism shown. The breakable monodose medicine package-supporting central member 205 has a shaft 225 and a piston 221 with the same type(s) of friction enhancing area 223 described anywhere above.

The central member 205 has a distal end adapted to support breakable monodose medicine package 217 so as to be positioned at (directly below) piercing spike 215. Central member 205 has piston shaft 225 with piston-engaging high friction area end and has a piston-releasing area distal end. Piston 221 located in the piston shaft 225, with piston 221 having a medicine container breaking distal end, having a central area with a high friction engaging surface to engage the proximal end of the piston shaft 225 and having an extended proximal end with flange 229, functionally connected to firing cap 211. The piston 221, in this embodiment, breaks the medicine container not by directly puncturing it, but by pushing it into spike 215, which breaks the container by puncture. The container 217 is a breakable plastic shell with liquid medicine therein. Firing cap 211 is connected to the proximal end of the central member 205 and is moveable toward the distal end of central member 205 by compressive force. The firing cap 211 has a piston-receiving cavity and a drive spring 209 located in the cavity. The extended proximal end of the piston 221 is functionally connected to the spring 209 as shown. Piston flange 229 is positioned under rim 227 and on spring 209, as shown.

There is a finger support means 207 located on the outside of central member 205. A child resistant locking mechanism includes the protrusions 231, 233 and 235 and operate similarly to the corresponding parts in FIG. 1. When locked, this prevents upward movement of the firing cap 211 toward the central member 205, and permits upward movement of the firing cap 211 toward the central member 205 when the locking member is unlocked.

The child resistant locking mechanism also performs as a post firing lock-up mechanism such that, once the device has been fired and the firing cap 211 has been advanced forward (upward) toward the central member 205, this locking mechanism is activated and locks up so as to prevent movement of the firing cap 211 away from the central member 205.

Figure 15:
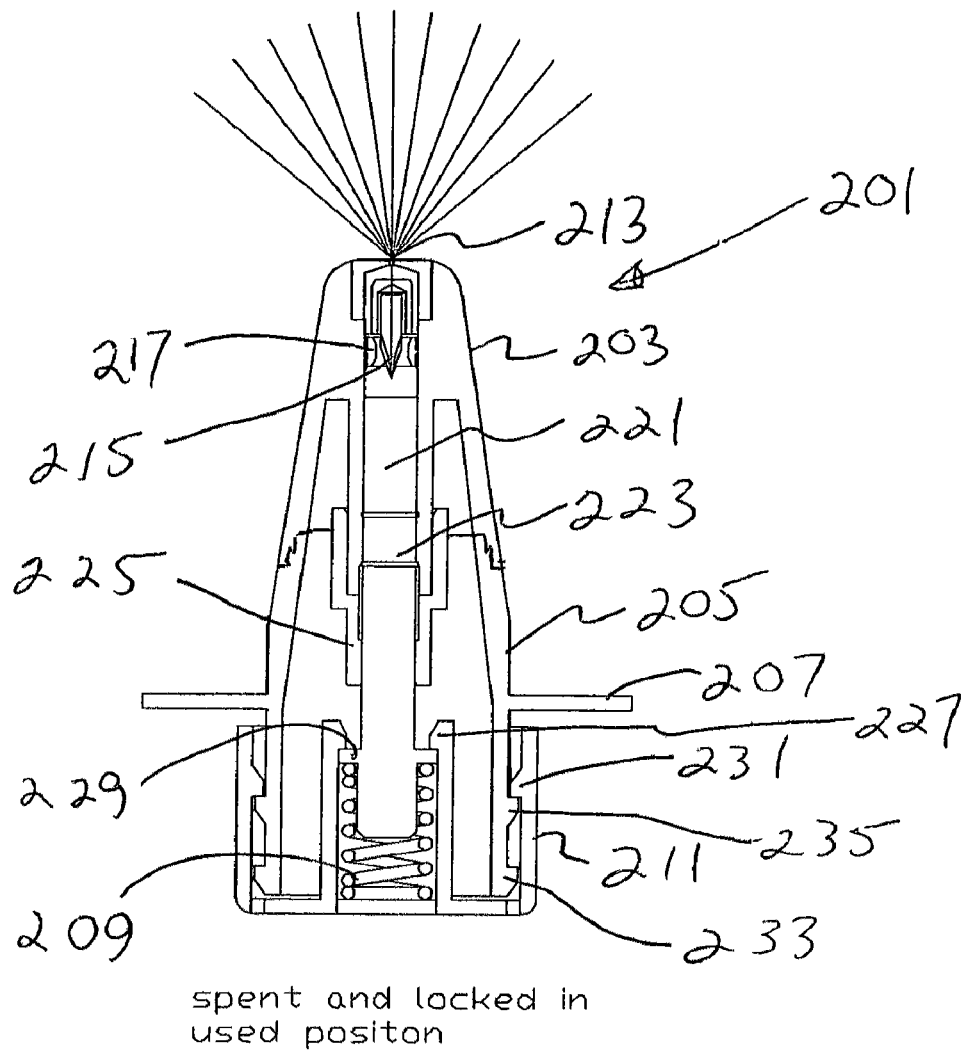
FIG. 15 shows the present invention monodose nasal sprayer of FIGS. 9, 10 and 11 in its just fired position.

In FIG. 12, the arrows shown in FIG. 10 are not lined up. Thus, the device is in the children resistant mode and cannot work. In FIGS. 13 and 14, the arrows have been lined up and the user has pushed the firing cap 211 toward the central member 205 to fully compress the spring 209, but not yet far enough to release the piston 221. In FIG. 15, the firing cap 211 has been advanced an additional 0.015 inches to pop the piston 221, pierce the container 217 and spray the medicine, as shown. It operates to drive medicine therefrom to and through the spray nozzle in a manner that is user independent as to dosage amount and dosage speed of delivery to yield a consistent, predetermined rate of dispensing and profile spray. The post firing lock-up mechanism automatically locks the device after use so that it cannot be refired.

Figure 16:
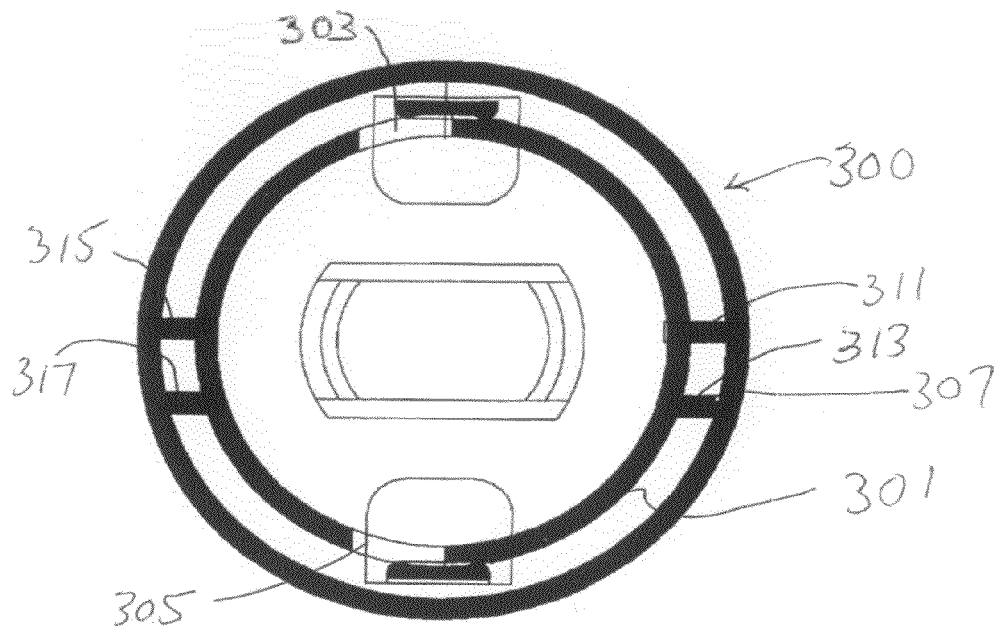
FIG. 16 is a cut bottom view of one embodiment of a rotating locking mechanism in its locked, child resistant position.
Figure 17:
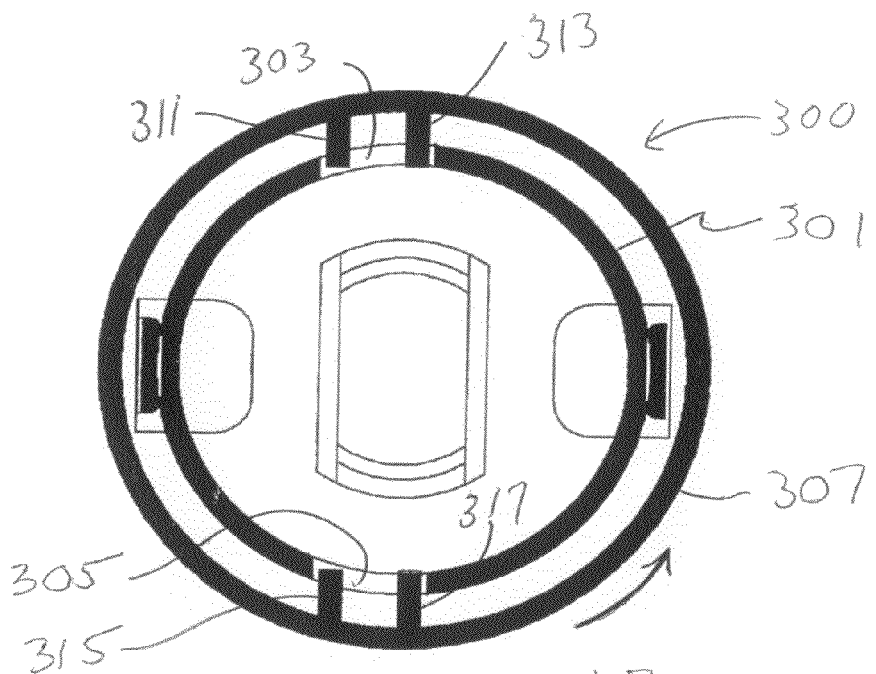
FIG. 17 is a cut bottom view of the rotating locking mechanism of FIG. 16 in its unlocked position ready for firing; and, FIGS. 18, 19, 20 and 21 illustrate another present invention embodiment wherein they show side cut views of the sprayer at different stages using a pierceable vial for the medicine container.

FIG. 16 is a cut bottom view of one embodiment of a rotating locking mechanism 300 in its locked, child resistant position. It shows a bottom view of a central member 301 with guide slots 3053 and 305, and of a firing cap 307 with inwardly projecting protrusions 311, 313, 315 and 317. In this FIG. 15, the guide slots and protrusions are not aligned and thus the firing cap 307 cannot be advanced. In FIG. 17, a cut bottom view of the rotating locking mechanism of FIG. 13 in its unlocked position ready for firing, they are aligned and the firing cap 307 may be advanced for firing.

FIGS. 18, 19, 20 and 21 illustrate another present invention embodiment sprayer 401 wherein they show side cut views of the sprayer 401 at different stages using a pierceable vial 409 for the medicine container. In all of these Figures, sprayer 401 has the three feature components, namely, main housing 403, central member 405 and firing cap 407. The internal aspects are similar to and operate in the same manner as those described in FIGS. 12 through 15 above. In this device, the medicine container is pierceable vial 409 and the spike 411 is also the outlet line to the exit nozzle. As can be seen in these Figures, when the piston strikes the vial 409, spike 411 pierces the vial membrane or otherwise breakable top, and then block 413 enters the vial 409 to displace the medicine, which rapidly exits as a spray through the nozzle.

Although particular embodiments of the invention have been described in detail herein with reference to the accompanying drawings, it is to be understood that the invention is not limited to those particular embodiments, and that various changes and modifications may be effected therein by one skilled in the art without departing from the scope or spirit of the invention as defined in the appended claims.

What is claimed is:

1. A monodose nasal sprayer device, which comprises:
   a.) an elongated main housing having a distal end adapted for partial insertion into one of a human nasal cavity and an animal nasal cavity and having a proximal end adapted to receive and hold a single use monodose medicine package-supporting central member, said elongated main housing having a spray discharge nozzle located at its distal end, said elongated main housing having medicine-receiving chamber connected to said nozzle and biased toward said single use monodose medicine package-supporting central member;
   b.) said single use medicine package-supporting central member being connected to said proximal end of said elongated main housing, said central member having a distal end adapted to support a single use monodose medicine package so as to be positioned at said chamber, and having a piston shaft with a piston-engaging high friction area end and having a piston-releasing area distal end;
   c.) a piston located in said piston shaft, said piston having a medicine container breaking distal end, having a central area with a high friction engaging surface to engage said proximal end of said piston shaft and having an extended proximal end functionally connected to a firing cap wherein said proximal end of said piston includes a flange that fits atop said spring and fits into said firing cap cavity;
   d.) a firing cap connected to said proximal end of said central member and being movable toward said distal end of said central member by compressive force, said firing cap having a piston-receiving cavity and a drive spring located in said cavity, said extended proximal end of said piston being functionally connected to said spring;
   e.) finger support means located on the outside of one of said main housing and said central member;
   f.) a child resistant inner locking mechanism connected to at least one of said central member and said firing cap that is unlockable and, when locked, prevents movement of said firing cap toward said distal end of said central member, and permits movement of said firing cap toward said distal end of said central member when said locking member is unlocked; and
   g.) a child resistant outer locking mechanism connected to said firing cap and said central member, adapted to prevent movement of said firing cap wherein said child resistant outer locking mechanism is a tear away system including a connection means for connecting said firing cap to said central member;
   wherein the force required to overcome the frictional force between said high-friction engaging surface of said piston and said piston shaft is greater than the force required to compress said spring; and,
   wherein a user may procure a monodose of medicine with said device when loaded with a single use monodose medicine package by (i) removing said outer locking mechanism so that its position is unlocked; (ii) moving said inner locking mechanism from its locked position to its unlocked position; and (iii) placing fingers in front of the finger support means and applying compressive force against said firing cap to move said firing cap towards said central member so as to compress said spring and to move said firing cap closer toward said central member to push said piston out of said piston engaging high friction area of said shaft so as to sufficiently reduce friction such that said spring automatically and with significant celerity, fires said piston and causes said distal end of said piston to puncture said single use monodose medicine package and to drive medicine therefrom to and through said spray nozzle in a manner that is user independent as to dosage amount and dosage speed of delivery to yield a consistent, predetermined profile spray.

2. The manually operated monodose nasal sprayer of claim 1 which includes a piercer attached to a proximal end of said single use monodose medicine package wherein when said piston is fired, said monodose medicine package moves upwardly to pierce said monodose medicine package and to drive medicine therefrom to and through said spray nozzle.

3. The manually operated monodose nasal sprayer of claim 2 wherein said piston shaft and said piston have corresponding circular peripheries from a top view.

4. The manually operated monodose nasal sprayer device of claim 2 wherein said distal end of said central member is connected to said proximal end of said main housing through connection means wherein said connection means is selected from one of the group consisting of corresponding screw components and corresponding snap components.

5. The manually operated monodose nasal sprayer device of claim 4 wherein said screw components include a one way locking thread stop so that said distal end of said central member and said proximal end of said main housing cannot be unscrewed once screwed together.

6. The manually operated monodose nasal prayer device of claim 5 wherein said piston shaft and said piston have corresponding circular peripheries from a top view.

7. The manually operated monodose nasal sprayer device of claim 6 wherein said outer locking mechanism connection means includes a perforated tab surrounding a circumference of at least one of said firing cap and said central member.

8. A monodose nasal sprayer device, which comprises:
   a.) an elongated main housing having a distal end adapted for partial insertion into one of a human nasal cavity and an animal nasal cavity and having a proximal end adapted to receive and hold a monodose medicine package-supporting central member, said elongated main housing having a spray discharge nozzle located at its distal end, said elongated main housing having a medicine-receiving chamber connected to said nozzle and biased toward said monodose medicine package-supporting central member;
   b.) said medicine package-supporting central member being connected to said proximal end of said elongated main housing, said central member having a distal end adapted to support a monodose medicine package so as to be positioned at said chamber, and having a piston shaft with a piston-engaging high friction area end and having a piston-releasing area distal end;
   c.) a piston located in said piston shaft, said piston having a medicine container breaking distal end, having a central area with a high friction engaging surface to engage said proximal end of said piston shaft and having an extended proximal end functionally connected to a firing cap wherein said proximal end of said piston includes a flange that fits atop said spring and fits into said firing cavity;
   d.) a firing cap connected to said proximal end of said central member and being movable toward said distal end of said central member by compressive force, said firing cap having a piston-receiving cavity and a drive spring located in said cavity, said extended proximal end of said piston being functionally connected to said spring;
   e.) finger support means located on the outside of one of said main housing and said central member;
   f.) a child resistant inner locking mechanism connected to at least one of said central member and said firing cap that is unlockable and, when locked, prevents movement of said firing cap toward said distal end of said central member, and permits movement of said firing cap toward said distal end of said central member when said locking member is unlocked; and
   g.) a plurality of dosage choice stops extending from said central member so that each stop may intersect a bar attached to said spring when said spring is decompressed and a corresponding monodose indicator is selected, said stops being different lengths adapted to meter a different predefined monodose and to stop movement of said spring such that when spring movement is stopped by a longer length stop said piston penetrates into a shorter distance within said monodose package thereby providing for less medicine to be dispensed when said monodose medicine package is punctured and when said spring movement is stopped by a shorter length stop said piston penetrates into a longer distance within said monodose package thereby providing for more said medicine to be dispensed when said monodose medicine package is punctured;
   wherein the force required to overcome the frictional force between said high friction engaging surface of said piston and said piston shaft is greater than the force required to compress said spring; and,
   wherein a user may procure a monodose of medicine with said device when loaded with a monodose medicine package by (i) moving said inner locking mechanism from its locked position to its unlocked position; (ii) selecting a metered monodose amount by rotating said central member to a monodose amount indicator so that said stop for said selected metered monodosage amount may intersect said bar of said spring, (iii) placing fingers in front of the finger support means and applying compressive force against said firing cap to move said firing cap towards said central member so as to compress said spring and to move said firing cap closer toward said central member to push said piston out of said piston engaging friction area of said shaft so as to sufficiently reduce friction such that said spring automatically and with significant celerity, fires said piston and causes said distal end of said piston to puncture said monodose medicine package and to drive medicine therefrom to and through said spray nozzle in a manner that is user independent as to dosage amount, once selected, and dosage speed of delivery to yield a consistent, predetermined profile spray.

9. The manually operated monodose nasal sprayer of claim 8 which said monodose medicine package includes a piercer attached to a proximal end of said single use monodose medicine package wherein when said piston is fired, said monodose medicine package moves upwardly to pierce said monodose medicine package and to drive medicine therefrom to and through said spray nozzle.

10. The manually operated monodose nasal sprayer device of claim 9 wherein said piston shaft and said piston have corresponding circular peripheries from a top view.

11. The manually operated monodose nasal sprayer of claim 9 wherein said distal end of said central member is connected to said proximal end of said main housing through connection means wherein said connection means is selected from the group consisting of corresponding screw components and corresponding snap components.

12. The manually operated nasal sprayer device of claim 9 wherein said screw components include a one way locking thread stop so that said distal end of said central member and said proximal end of said main housing cannot be unscrewed once screwed together.

13. The manually operated monodose nasal sprayer device of claim 12 wherein said piston shaft and said piston have corresponding circular peripheries from a top view.

14. The manually operated monodose nasal sprayer device of claim 10 wherein said inner locking mechanism is a rotating locking mechanism with a first position being a lock position to inhibit advancement of said firing cap and a second position being an unlock position to permit advancement of said firing cap, said second position being located at an arc of a predetermined distance from said first position.

15. A monodose nasal sprayer device, which comprises:
   a.) an elongated main housing having a distal end adapted for partial insertion into one of a human nasal cavity and an animal nasal cavity and having a proximal end adapted to receive and hold a single use monodose medicine package-supporting central member, said elongated main housing having a spray discharge nozzle located at its distal end, said elongated main housing having a medicine-receiving chamber connected to said nozzle and biased towards said single use monodose medicine package-supporting central member;

b.) said single use medicine package-supporting central member being connected to said proximal end of said elongated main housing, said central member having a distal end adapted to support a single use monodose medicine package so as to be positioned at said chamber, and having a piston shaft with a piston-engaging high friction area end and having a piston-releasing area distal end;

c.) a proximal end plug cap piston located in said piston shaft, said proximal end plug cap piston having a medicine container breaking distal end plug cap piston, having a central area with a high friction engaging surface to engage said proximal end of said piston shaft and having an extended proximal end functionally connected to a firing cap wherein said proximal end of said piston includes a flange that fits atop said spring and fits into said firing cap cavity;

d.) a firing cap connected to said proximal end of said central member and being moveable toward said distal end of said central member by compressive force, said firing cap having a piston-receiving cavity and a drive spring located in said cavity, said extended proximal end of said piston being functionally connected to said spring;

e.) finger support means located on the outside of one of said main housing and said central member;

f.) a child resistant inner locking mechanism connected to at least one of said central member and said firing cap that is unlockable and, when locked, prevents movement of said firing cap toward said distal end of said central member, and permits movement of said firing cap toward said distal end of said central member when said locking member is unlocked; and g.) said single use monodose medicine package including said proximal end plug cap piston and said distal end plug cap piston wherein when said firing cap is fired and said spring pushes said proximal end plug cap piston into said distal end plug cap piston thereby driving said medicine through said spray nozzle;

wherein the force required to overcome the frictional force between said high friction engaging surface of said proximal end plug cap piston and said piston shaft is greater than the force required to compress said spring; and, wherein a user may procure a monodose of medicine with said device when loaded with a single use monodose medicine package by (i) moving said inner locking mechanism from its locked position to its unlocked position; (ii) placing fingers in front of the finger support means and applying compressive force against said firing cap to move said firing cap toward said central member so as to compress said spring and to move said firing cap closer toward said central member to push said proximal end plug cap piston out of said piston engaging friction area of said shaft so as to sufficiently reduce friction such that said spring automatically and with significant celerity, fires said piston and causes said distal end of said piston to force said proximal end plug cap to move as a piston through said single use monodose medicine package and to force said distal end plug cap to be removed from the plug and to move as a piston thereby driving said medicine therefrom to and through said spray nozzle in a manner that is user independent as to dosage amount and dosage speed of delivery to yield a consistent, predetermined profile spray.

16. The manually operated monodose nasal sprayer device of claim 15 wherein said piston shaft and said piston have corresponding circular peripheries from a top view.

17. The manually operated monodose nasal sprayer device of claim 15 wherein said distal end of said central member is connected to said proximal end of said main housing through connection means wherein said connection means is selected from the group consisting of corresponding screw components and corresponding snap components.

18. The manually operated monodose nasal sprayer device of claim 17 wherein said screw components include a one way locking thread stop so that said distal end of said central member and said proximal end of said main housing cannot be unscrewed once screwed together.

19. The manually operated monodose nasal sprayer device of claim 18 wherein said piston shaft and said piston have corresponding circular peripheries from a top view.

20. The manually operated monodose nasal sprayer device of claim 16 wherein said inner locking mechanism is a rotating locking mechanism with a first position being a lock position to inhibit advancement of said firing cap and a second position being an unlock position to permit advancement of said firing cap, said second position being located at an arc of a predetermined distance from said first position.

* * * * *